United States Patent
Grady et al.

(10) Patent No.: US 12,387,849 B2
(45) Date of Patent: *Aug. 12, 2025

(54) SYSTEMS AND METHODS FOR VESSEL REACTIVITY TO GUIDE DIAGNOSIS OR TREATMENT OF CARDIOVASCULAR DISEASE

(71) Applicant: HeartFlow, Inc., Redwood City, CA (US)

(72) Inventors: Leo Grady, Darien, CT (US); Charles A. Taylor, Atherton, CA (US); Christopher K. Zarins, Austin, TX (US)

(73) Assignee: Heartflow, Inc., Mountain View, CA (US)

( * ) Notice: Subject to any disclaimer, the term of this patent is extended or adjusted under 35 U.S.C. 154(b) by 1186 days.

This patent is subject to a terminal disclaimer.

(21) Appl. No.: 17/201,589

(22) Filed: Mar. 15, 2021

(65) Prior Publication Data

US 2021/0202110 A1 Jul. 1, 2021

Related U.S. Application Data

(63) Continuation of application No. 15/434,578, filed on Feb. 16, 2017, now Pat. No. 10,978,210, which is a continuation of application No. 15/017,295, filed on Feb. 5, 2016, now Pat. No. 9,607,130, which is a continuation of application No. 14/592,546, filed on Jan. 8, 2015, now Pat. No. 9,292,659.

(60) Provisional application No. 62/072,256, filed on Oct. 29, 2014.

(51) Int. Cl.
| | |
|---|---|
| G16H 50/50 | (2018.01) |
| A61B 5/00 | (2006.01) |
| A61B 5/02 | (2006.01) |
| A61B 5/026 | (2006.01) |
| G16H 20/10 | (2018.01) |
| G16H 20/40 | (2018.01) |
| G16H 50/20 | (2018.01) |

(52) U.S. Cl.
CPC ......... *G16H 50/50* (2018.01); *A61B 5/02007* (2013.01); *A61B 5/026* (2013.01); *A61B 5/7267* (2013.01); *G16H 50/20* (2018.01); *G16H 20/10* (2018.01); *G16H 20/40* (2018.01)

(58) Field of Classification Search
None
See application file for complete search history.

(56) References Cited

U.S. PATENT DOCUMENTS

| 8,315,812 B2 | 11/2012 | Taylor |
| 2012/0084064 A1 | 4/2012 | Dzenis et al. |
| 2015/0297098 A1 | 10/2015 | Gurfinkel |

FOREIGN PATENT DOCUMENTS

| JP | 2014-188161 | 10/2014 |
| WO | WO 2013/138428 A1 | 9/2013 |
| WO | WO 2014/081348 A1 | 5/2014 |
| WO | WO 2015/148401 A1 | 10/2015 |

OTHER PUBLICATIONS

Kim et al. (Annals of Biomedical Engineering, vol. 38, No. 10, Oct. 2010 ( 2010) pp. 3195-3209).*
Baek et al. (Computer Methods in Applied Mechanics and Engineering (2007) vol. 196:3070-3078).
Figueroa et al. (Computer Methods in Applied Mechanics and Engineering (2009) vol. 198:3583-3602).
Kim et al. (Computer Methods in Applied Mechanics and Engineering (2009) vol. 198:3551-3566).
Masson et al. (Computer Methods in Applied Mechanics and Engineering (2009) vol. 198:3551-3566).
Pekkan et al. (Med. Biol. Eng. Comput. (2008) vol. 46:1139-1152).
Steele et al. (IEEE Transaction on Information tech. in Biomedicine (2003) vol. 7:123-129.
Taylor et al. (Computer Methods in Applied Mechanics and Engineering (2009) vol. 198:3514-3523).
Tezduyar et al. (Computer Methods in Applied Mechanics and Engineering (2009) vol. 198:3524-3533).
Torii et al. (Computer Methods in Applied Mechanics and Engineering (2009) vol. 198:3613-3621).
International Search Report and Written Opinion for corresponding Application No. PCT/US2015/057754, dated Feb. 16, 2016 (15 pages).
Robert Schier et al.: "Brachial artery reactivity and vascular reactive hyperemia for preoperative anaesthesia risk assessment ? an observational study", BMC Anesthesiology, Biomed Central, London, GB, vol. 14, No. 1, Jun. 21, 2014 (Jun. 21, 2014), p. 47, XP021189075, ISSN: 1471-2253, DOI: 10.1186/1471-2253-14-47 abstract p. 1, right-hand column line 9—p. 2, left-hand column line 4 subsections "Brachial Artery Reactivity Testing (BART)" on p. 3 and "BART-strengths and weaknesses" on p. 6.

* cited by examiner

*Primary Examiner* — Lori A. Clow
(74) *Attorney, Agent, or Firm* — Bookoff McAndrews, PLLC (57) ABSTRACT

Systems and methods are disclosed for using vessel reactivity to guide diagnosis or treatment for cardiovascular disease. One method includes receiving a patient-specific vascular model of a patient's anatomy, including at least one vessel of the patient; determining, by measurement or estimation, a first vessel size at one or more locations of a vessel of the patient-specific vascular model at a first physiological state; determining a second vessel size at the one or more locations of the vessel of the patient-specific vascular model at a second physiological state using a simulation or learned information; comparing the first vessel size to the corresponding second vessel size; and estimating a characteristic of the vessel of the patient-specific vascular model based on the comparison.

20 Claims, 5 Drawing Sheets

SYSTEMS AND METHODS FOR VESSEL REACTIVITY TO GUIDE DIAGNOSIS OR TREATMENT OF CARDIOVASCULAR DISEASE

RELATED APPLICATION(S)

This application is a continuation of U.S. patent application Ser. No. 15/434,578, filed Feb. 16, 2017, which is a continuation of U.S. patent application Ser. No. 15/017,295 (now U.S. Pat. No. 9,607,130), filed Feb. 5, 2016, which is a continuation of U.S. patent application Ser. No. 14/592,546 (now U.S. Pat. No. 9,292,659), filed Jan. 8, 2015, which claims the benefit of priority from U.S. Provisional Application No. 62/072,256, filed on Oct. 29, 2014, which are incorporated by reference herein in their entireties.

FIELD OF THE DISCLOSURE

Various embodiments of the present disclosure relate generally to disease assessment, treatment planning, and related methods. More specifically, particular embodiments of the present disclosure relate to systems and methods for using vessel reactivity to guide diagnosis or treatment for cardiovascular disease.

BACKGROUND

Coronary artery disease is a common ailment that affects millions of people. Coronary artery disease may cause the blood vessels providing blood to the heart to develop lesions, such as a stenosis (abnormal narrowing of a blood vessel). As a result, blood flow to the heart may be restricted. A patient suffering from coronary artery disease may experience chest pain, referred to as chronic stable angina during physical exertion or unstable angina when the patient is at rest. A more severe manifestation of disease may lead to myocardial infarction, or heart attack. Significant strides have been made in the treatment of coronary artery disease including both medical therapy (e.g. statins) or surgical alternatives (e.g., percutaneous coronary intervention (PCI) and coronary artery bypass graft surgery (CABG)). Invasive assessments are commonly used to assess the type of treatment a patient may receive. However, indirect or noninvasive assessments for formulating a patient treatment are being explored and developed.

Heart disease is typically viewed as resulting from vessel disease, in particular, narrowing or blockage inside vessel lumens in a way that impacts blood flow. Currently, treatment assessment takes into account such intraluminal factors. Meanwhile, vessel size, itself, may also fluctuate. For example, healthy vessels may change size in response to various physiological states in a manner that differs from that of a diseased vessel. The discrepancy in response between healthy vessels and diseased vessels may serve as an indicator of the severity of a disease. Thus, a desire exists for understanding how severity of cardiovascular disease may be inferred from changes in vessel size in response to different physiological states. Furthermore, a desire exists to improve treatment of cardiovascular disease by better assessing the severity of cardiovascular disease.

The foregoing general description and the following detailed description are exemplary and explanatory only and are not restrictive of the disclosure.

SUMMARY

According to certain aspects of the present disclosure, systems and methods are disclosed for using vessel reactivity to guide diagnosis or treatment of cardiovascular disease. One method includes: receiving a patient-specific vascular model of a patient's anatomy, including at least one vessel of the patient; determining, by measurement or estimation, a first vessel size at one or more locations of a vessel of the patient-specific vascular model at a first physiological state; determining a second vessel size at the one or more locations of the vessel of the patient-specific vascular model at a second physiological state using a simulation or learned information; comparing the first vessel size to the corresponding second vessel size; and estimating a characteristic of the vessel of the patient-specific vascular model based on the comparison.

In accordance with another embodiment, a system for using vessel reactivity in diagnosing or treating disease comprises: a data storage device storing instructions for using vessel reactivity in diagnosing or treating disease; and a processor configured for: receiving a patient-specific vascular model of a patient's anatomy, including at least one vessel of the patient; determining, by measurement or estimation, a first vessel size at one or more locations of a vessel of the patient-specific vascular model at a first physiological state; determining a second vessel size at the one or more locations of the vessel of the patient-specific vascular model at a second physiological state using a simulation or learned information; comparing the first vessel size to the corresponding second vessel size; and estimating a characteristic of the vessel of the patient-specific vascular model based on the comparison.

In accordance with another embodiment, a non-transitory computer readable medium for use on a computer system containing computer-executable programming instructions for performing a method of using vessel reactivity in diagnosing or treating disease, the method comprising: receiving a patient-specific vascular model of a patient's anatomy, including at least one vessel of the patient; determining, by measurement or estimation, a first vessel size at one or more locations of a vessel of the patient-specific vascular model at a first physiological state; determining a second vessel size at the one or more locations of the vessel of the patient-specific vascular model at a second physiological state using a simulation or learned information; comparing the first vessel size to the corresponding second vessel size; and estimating a characteristic of the vessel of the patient-specific vascular model based on the comparison.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments, and together with the description, serve to explain the principles of the disclosed embodiments.

DESCRIPTION OF THE EMBODIMENTS

Reference will now be made in detail to the exemplary embodiments of the disclosure, examples of which are illustrated in the accompanying drawings. Wherever possible, the same reference numbers will be used throughout the drawings to refer to the same or like parts.

Coronary artery disease is a common ailment, by which blood flow to the heart may be restricted. While significant strides have been made in the treatment of coronary artery disease, the treatment is often misplaced or excessive. For example, patients often undergo invasive surgical treatments when medication may suffice. Patients are sometimes subjected to treatments that may not change their condition. In some situations, patients even undergo treatments that ultimately worsen their condition. Thus, a need exists to accurately assess the severity of cardiovascular disease in selecting a course of treatment.

Cardiovascular disease may be linked to vessel disease, meaning vessel narrowing or blockage. While cardiovascular disease analysis often focuses on intraluminal factors, vessel size is itself not static. Rather, vessels may change in size during different physiological states. For example, vessel size may change to accommodate more or less blood flow in response to signals from the sympathetic and parasympathetic nervous systems that regulate blood flow demand. An inadequate change in vessel size may reflect disease severity, either locally or systemically. In other words, vascular disease may be inferred where vessel size change deviates from expected changes in vessel size. Furthermore, measurement of size changes may help a physician determine the severity of cardiovascular disease. The extent to which a vessel changes size in response to changes in physiological state, may be referred to as, "vessel reactivity." In addition, vessel size reactivity may impact blood flow. For instance, dilated vessels may carry more blood flow in response to tissue demand, meaning that some lesions that do not significantly impede blood flow during rest may significantly reduce blood flow during a high-demand state, e.g., hyperemia.

Therefore, an understanding of the change in vessel size may be clinically important. An understanding of vessel reactivity may improve an evaluation of the severity of disease and of the appropriateness of treatment. The present disclosure may benefit patients and doctors by either estimating vessel reactivity under conditions in which vessel reactivity may be difficult to measure, and/or by employing measurements of vessel reactivity to more accurately assess the severity of vessel disease in different physiological conditions.

Figure 1:
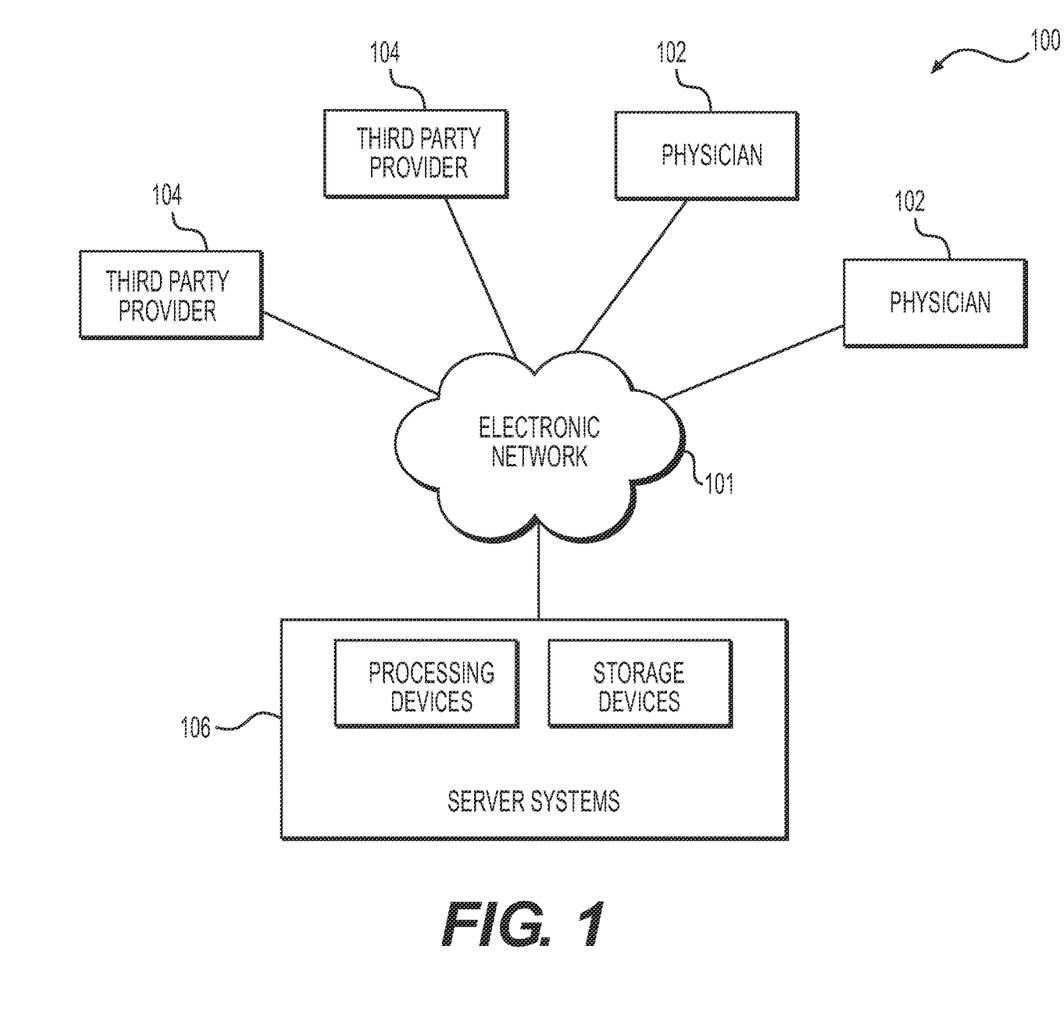
FIG. 1 is a block diagram of an exemplary system and network for using vessel reactivity to guide diagnosis or treatment of cardiovascular disease, according to an exemplary embodiment of the present disclosure.

Referring now to the figures, FIG. 1 depicts a block diagram of an exemplary system 100 and network for using vessel reactivity to guide diagnosis or treatment of cardiovascular disease, according to an exemplary embodiment. Specifically, FIG. 1 depicts a plurality of physicians 102 and third party providers 104, any of whom may be connected to an electronic network 101, such as the Internet, through one or more computers, servers, and/or handheld mobile devices. Physicians 102 and/or third party providers 104 may create or otherwise obtain images of one or more patients' anatomy. The physicians 102 and/or third party providers 104 may also obtain any combination of patient-specific information, such as age, medical history, blood pressure, blood viscosity, patient activity or exercise level, etc. Physicians 102 and/or third party providers 104 may transmit the anatomical images and/or patient-specific information to server systems 106 over the electronic network 101. Server systems 106 may include storage devices for storing images and data received from physicians 102 and/or third party providers 104. Server systems 106 may also include processing devices for processing images and data stored in the storage devices.

Figure 2:
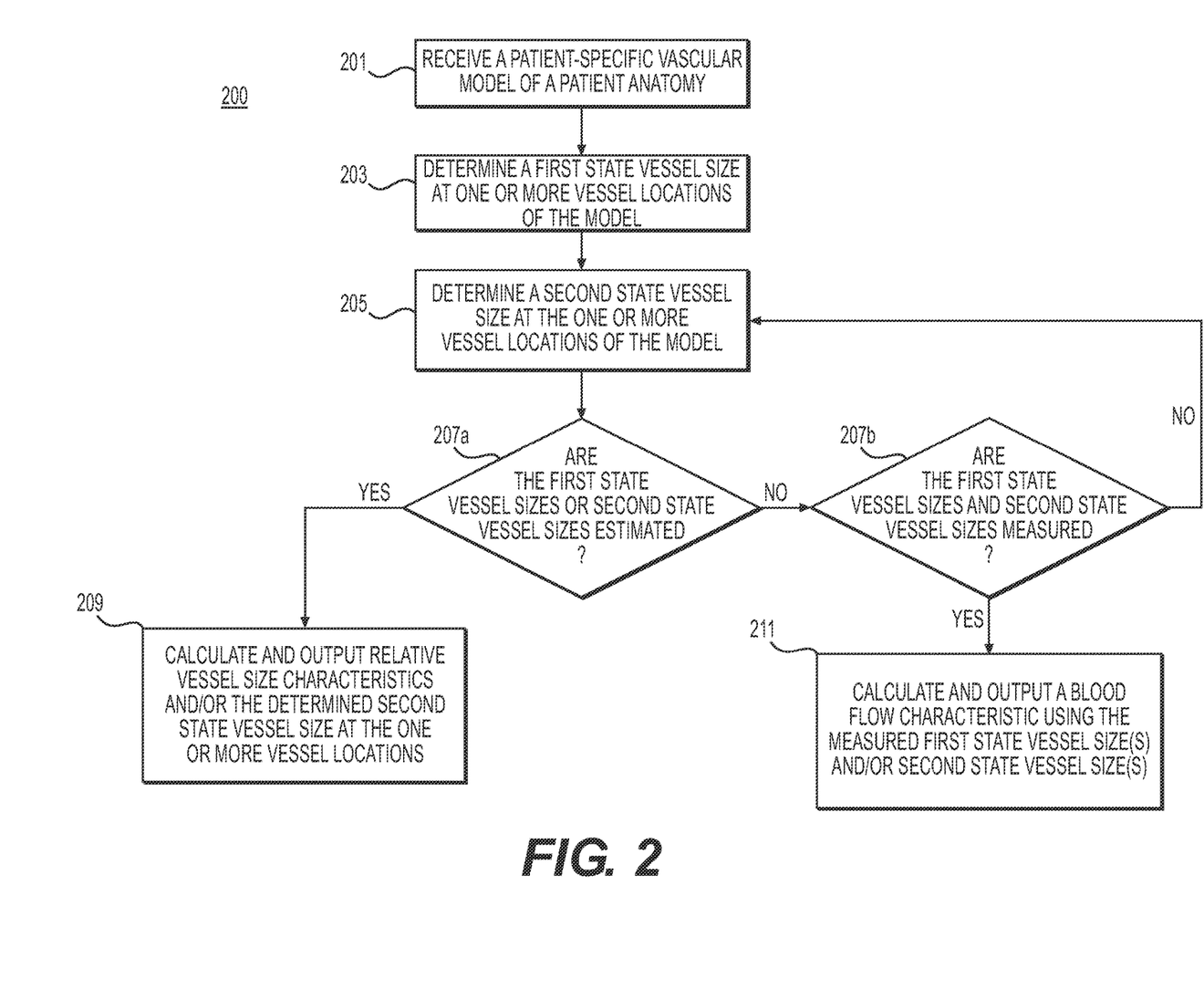
FIG. 2 is a block diagram of an exemplary method of using vessel reactivity to guide diagnosis or treatment of cardiovascular disease, according to an exemplary embodiment of the present disclosure.
Figure 3A:
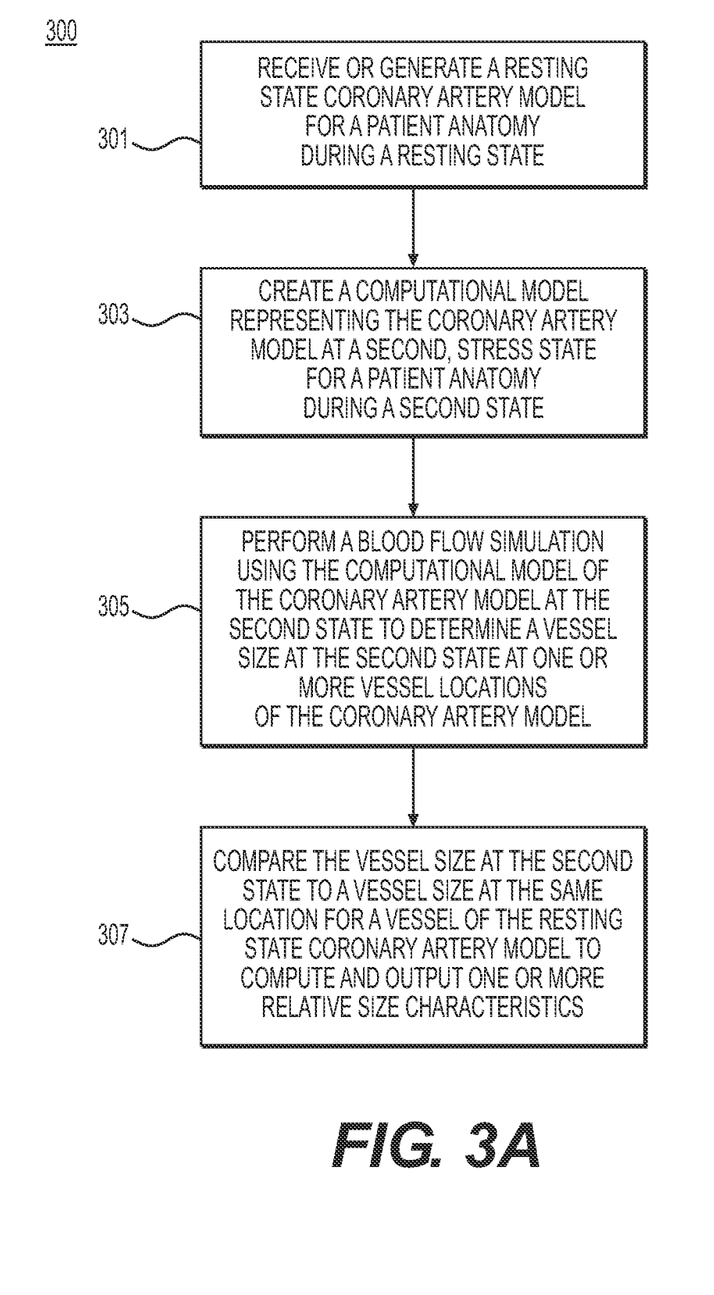
FIG. 3A is a block diagram of an exemplary method of estimating coronary artery reactivity, according to an exemplary embodiment of the present disclosure.
Figure 3B:
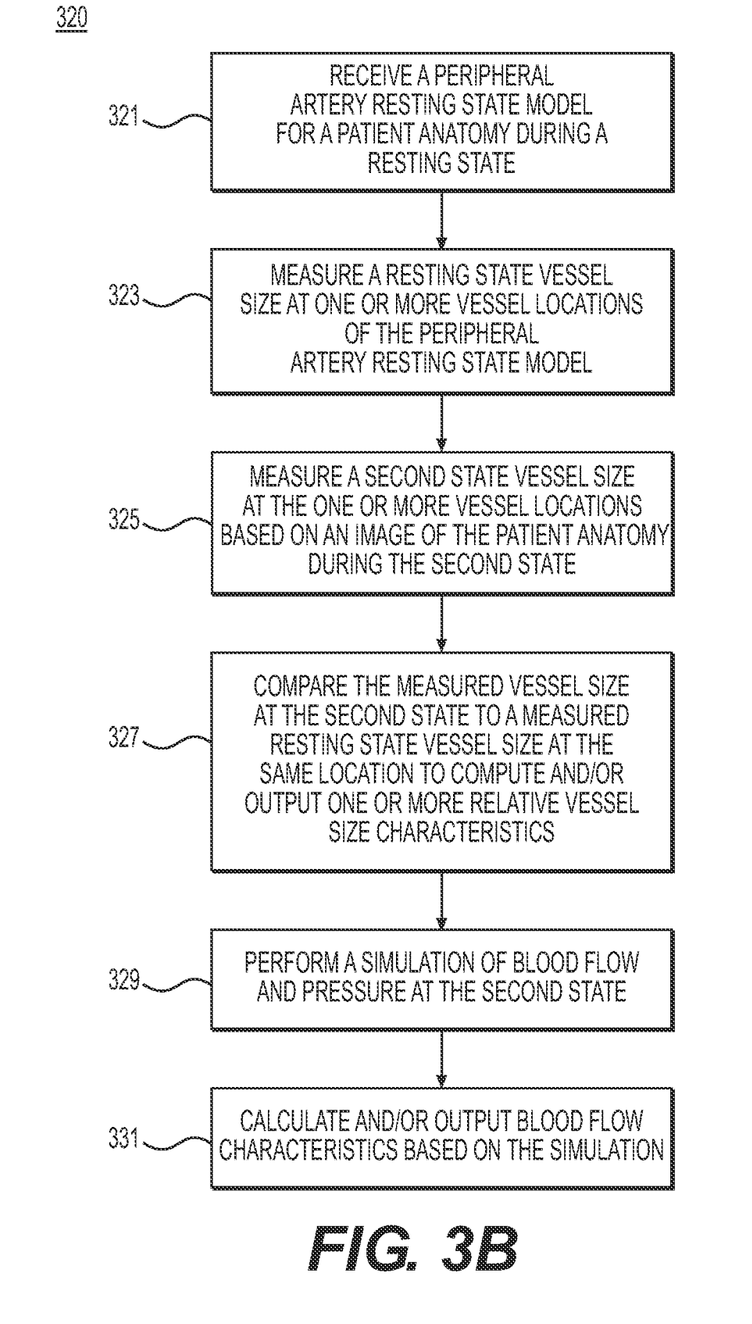
FIG. 3B is a block diagram of an exemplary method of using vessel reactivity to inform a simulation of peripheral artery disease (PAD), according to an exemplary embodiment of the present disclosure.
Figure 3C:
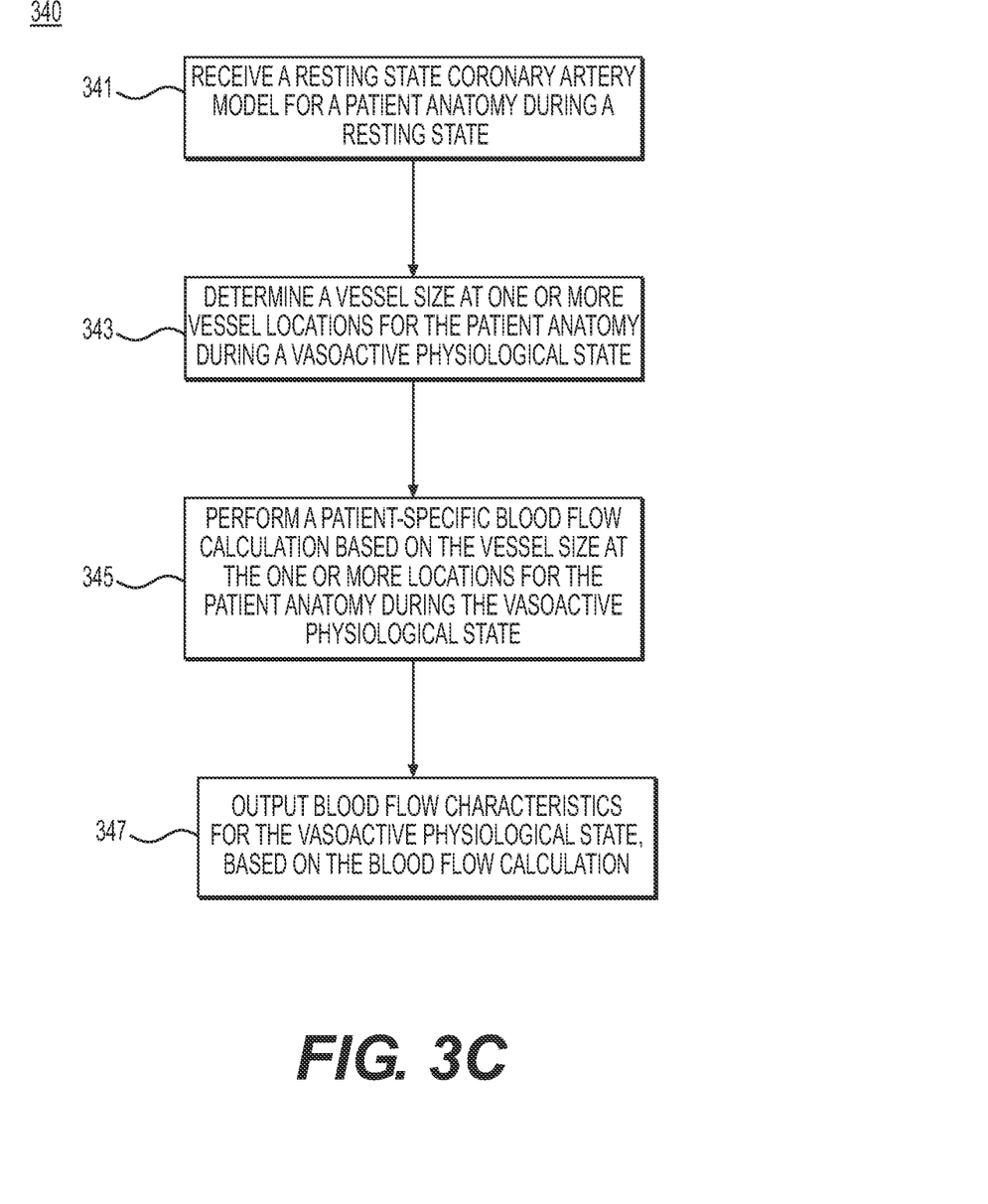
FIG. 3C is a block diagram of an exemplary method of taking vessel reactivity into account in modeling drug effects, according to an exemplary embodiment of the present disclosure.

FIG. 2 depicts a general embodiment of a method for using vessel reactivity to guide diagnosis or treatment of cardiovascular disease. FIGS. 3A-3C depict exemplary embodiments of the method of FIG. 2. For example, FIG. 3A depicts an embodiment of a process for estimating coronary reactivity. FIG. 3B depicts an embodiment of a process for using vessel reactivity to inform a simulation of peripheral artery disease. FIG. 3C depicts an embodiment of a process for using vessel reactivity in modeling drug effects.

FIG. 2 is a block diagram of an exemplary method 200 of using vessel reactivity to guide diagnosis or treatment of cardiovascular disease, according to an exemplary embodiment. The method of FIG. 2 may be performed by server systems 106, based on information, images, and data received from physicians 102 and/or third party providers 104 over electronic network 101.

In one embodiment, step 201 may include receiving a patient-specific anatomic model in an electronic storage medium of the server systems 106. Specifically, receiving the patient-specific anatomic model may include either generating the patient-specific anatomic model at the server system 106, or receiving one over an electronic network (e.g., electronic network 101). The patient-specific anatomic model may include a cardiovascular model of a specific person. In one embodiment, the anatomic model may be derived from images of the person acquired via one or more available imaging or scanning modalities (e.g., computed tomography (CT) scans and/or magnetic resonance imaging (MRI)). For example, step 201 may include receiving CT and/or MRI images of a person's heart. Step 201 may further include generating, from the received images, a patient-specific cardiovascular model for the particular person. For the purposes of the disclosure, "patient" may refer to any individual or person for whom diagnosis or treatment analysis is being performed, or any individual or person associated with the diagnosis or treatment analysis of one or more individuals.

In one embodiment, step 203 may include determining a vessel size at one or more vessel locations of the patient-specific anatomic model for a person, while the person is in a resting state. This determination may be based on a measurement (e.g., by measuring vessel diameter from imaging) or via an estimation of vessel size in a resting state (e.g., based on a three-dimensional (3D) simulation, a one-dimensional (1D) simulation, or a learned relationship).

In one embodiment, step 205 may include determining a vessel size at one or more vessel locations of the person, while the person is in a physiological state other than the resting state, or a "second" physiological state. One instance of such a physiological state may include hyperemia. Thus, step 205 may include determining a vessel size at one or more vessel locations of the person's anatomy, while the person is in a hyperemic state. This determination may also be based on a measurement of vessel size (e.g., by measuring vessel diameter from imaging) or via an estimation of vessel size in a resting state (e.g., based on a three-dimensional (3D) simulation, a one-dimensional (1D) simulation, or a learned relationship). In one embodiment, step 205 may further include determining, specifying, and/or selecting a physiological state as the "second physiological state" in comparing vessel sizes at a physiological state different from a patient resting state.

In one embodiment, step 207a and step 207b may include categorizing the determined vessel sizes from steps 203 and 205, depending on whether the determined sizes were estimated or computed. For example, step 207a may include determining if either of steps 203 or 205 were computed. Step 209 may include outputting the estimated sizes, if the vessel sizes at either of steps 203 or 205 were determined by estimation (e.g., computed). Step 209 may further include outputting other relative size characteristics (e.g., characteristics determined from a comparison of a vessel size at one state against a vessel size at a corresponding vessel location at another state, for instance, reactivity or flow-mediated dilation). In one embodiment, step 209 may include determining the relative size characteristics from comparing the determined, e.g., resting state, vessel size(s) from step 203 against corresponding, e.g., hyperemic, vessel size(s) determined from step 205. The output may be displayed to a user and/or stored, e.g., in an electronic storage medium.

In one embodiment, step 211 may include producing an output if the vessel sizes at both steps 203 and 205 were determined by measurement (e.g., step 207b, "yes"). For example, step 211 may include determining a relationship in vessel sizes in order to estimate vessel resistance of the entire vessel and/or at each of the one or more vessel locations where vessel sizes were measured for steps 203 and 205. Step 211 may further include calculating a blood flow characteristic using the estimated vessel resistance (e.g., based on a 3D simulation, 1D simulation, or a learned relationship). Step 211 may then include outputting the calculated blood flow characteristic, e.g., to an electronic storage medium. The output may include stored data or a presentation of the information (e.g., a rendering that may receive and/or prompt user input and user interaction).

In one embodiment, method 200 may further include treatment analysis. For example, output from step 211 may be used to compare several treatments, where each second state may embody a treatment (e.g., various types of medication). Furthermore, method 200 may include using the comparison to select a treatment for a patient, either for the person for which the patient-specific anatomic model was constructed (e.g., in step 201) or for another patient (e.g., a patient with characteristics or circumstances similar to the person modeled in step 201).

FIG. 3A is a block diagram of an exemplary method 300 of estimating coronary reactivity, according to an exemplary embodiment. The method of FIG. 3A may be performed by server systems 106, based on information, images, and data received from physicians 102 and/or third party providers 104 over electronic network 101.

In one embodiment, vessel reactivity may be easier to measure in some areas of a person's vasculature than in other areas of the person's vasculature (e.g., coronaries and intracranial vessels), especially when attempting to measure the vessel reactivity in multiple physiological states. A measurement of vessel reactivity may be desirable, but difficult to obtain. As a result, method 300 may provide a method for determining the coronary reactivity by estimation, e.g., 3D simulation.

In one embodiment, step 301 may include receiving or generating (e.g., from CT and/or MRI images) a coronary artery model of a person in a resting state. For example, the model may include a 3D mesh model or a 1D reduced order model. This coronary artery model may be obtained, e.g., via segmentation of a cardiac CT image of the patient. Step 301 may further include storing the model in an electronic storage medium of server systems 106.

In one embodiment, steps 303 and 305, in combination, may include determining a vessel size at one or more vessel locations of the person's coronary artery for the person in a non-resting physiological state (e.g., hyperemia, various levels of exercise, post prandial, positional (e.g., supine-upright), gravitational (e.g., G-forces, zero gravity, etc.), emotional stress, hypertension, etc.). In one embodiment, step 303 may include identifying or selecting a physiological state as the "second state." In some instances, the second state may also be referred to as a stress state.

In one embodiment, performing step 303 may include modeling the non-resting physiological state (e.g., a stress state), for instance, with a reduction in epicardial resistance. Such modeling may include creating a computational model representing the stress state. Step 305 may include performing a 3D fluid-structure blood flow simulation using the modeled stress state. The simulation may model how changes in flow and pressure affect passive response characteristics of the vessel. For example, modeling passive mechanical response of a vessel wall may include using elastic or viscoelastic constitutive equations and modeling the vessel wall as a rigid, static wall. For instance, a patient in a hyperemic state may have a simulation assuming maximum vessel dilation throughout the simulation.

Alternately or in addition, the simulation may include modeling the vessel wall as a dynamic (rather than a static) entity. For example, the simulation may involve modeling active response characteristics of the vessel wall (e.g., including smooth muscle tone) in responding to changes in flow and pressure. In modeling active response characteristics, elastic or viscoelastic properties may be further based on tension induced by partial or full contraction of smooth muscle cells in a vessel wall (e.g., thereby increasing tension in a the vessel wall). For example, vessels may undergo spasms that cause tension in the vessel wall to fluctuate. Modeling active response characteristics may include accounting for dynamic changes to blood vessel sizes, dimensions, and deformation characteristics when under different physiological states. In one embodiment, the blood flow simulation of step 305 may be performed using a computing processor.

In one embodiment, step 307 may include outputting, e.g., to an electronic storage medium, characteristics of the relative size or resultant vessel size in simulated hyperemia or exercise (e.g., vessel diameter, reactivity, response to changes in pressure, or flow-mediated dilation). For instance, step 307 may include a comparison of the initial (e.g., resting state) coronary artery model vessel radius to a radius of a simulated vessel (e.g., calculated in response to an altered physiological state or stress state).

FIG. 3B is a block diagram of an exemplary method 320 of using vessel reactivity to inform a simulation of peripheral artery disease (PAD), according to an exemplary embodiment. The method of FIG. 3B may be performed by server systems 106, based on information, images, and data received from physicians 102 and/or third party providers 104 over electronic network 101.

Blood flow simulation may provide a mechanism for performing a non-invasive assessment of disease severity (e.g., plaque, stenosis, etc.). One example may include the simulation of fractional flow reserve (FFR), which may be measured under hyperemic conditions. Since noninvasive scans, e.g., CT, MR, or ultrasound (whether 2D or 3D), may be acquired under rest conditions, accurately performing a blood flow simulation under hyperemic or exercise conditions may include population-based assumptions of changes in vessel resistance, as well as responses to changes in pressure and flow. Measuring vessel reactivity may provide a means to improve the accuracy of a blood flow simulation by using a patient-specific estimate of vessel resistance at hyperemic or exercise states, or any other physiological states.

Step 321 may include receiving a peripheral artery model of a person in a resting state, e.g., in an electronic storage medium. Examples of such a model may include a 3D mesh model or a 1D reduced order model. The peripheral artery model may be obtained, e.g., via segmentation of a CT angiography (CTA) or magnetic resonance angiography (MRA) image for the person, while the person is in a resting state. Step 321 may further include receiving or calculating a resting state peripheral resistance for the peripheral artery model of the person.

Step 323 may include determining, by measurement, a vessel size at one or more vessel locations of the person's peripheral vascular system, while the person is in a resting physiological state. For example, step 323 may include measuring the size of a vessel at a selected location in the received resting state peripheral artery model (e.g., from step 321). In one embodiment, this measurement may be obtained from the peripheral artery model or measured directly from an image, e.g., a CT, MR, 2D ultrasound, or 3D ultrasound.

Step 325 may include determining, by measurement, a vessel size at one or more vessel locations of the person, while the person is in a non-resting physiological state (e.g., hyperemia, various levels of exercise, etc.). In one embodiment, this determination may be obtained directly from an image (e.g., CTA, MRA, or ultrasound data).

Steps 327 and 329 may include performing a blood flow characteristic calculation (e.g., of flow and/or pressure) using the change in size of the vessel at the one or more vessel locations of the person's peripheral vascular system to inform a patient-specific vessel resistance change observed when the person is in a hyperemic state. For example, step 327 may include calculating a patient-specific vessel resistance from a comparison of the vessel sizes found in steps 323 and 325. Step 327 may be performed, for example, by computing the ratio of a vessel size at a vessel location at resting state versus the vessel size at that same vessel location at a hyperemic state, for at least a portion of each of the vessel locations measured. In one embodiment, step 327 may include averaging the computed ratios to obtain at least one average ratio to represent an average vessel reactivity across (all or the at least a portion of) the vessel locations where vessel size was measured.

Step 329 may include performing a 3D simulation of blood flow and pressure for the person in a hyperemic state, using the average ratio. In one embodiment, this simulation may include extracting an anatomic and physiologic model of the patient based on the resting state model (e.g., from step 301). The simulation may further include modeling the mechanical effect of hyperemic pressure acting on the vessel wall and/or the response of the smooth muscle tone or active state of the vessel wall to pharmacologic drugs used to induce hyperemia. For example, step 329 may include dividing the resting state peripheral resistance by the average ratio (obtained via the measurements of steps 323 and 325, and then computed in step 327) in order to perform the 3D simulation representing a peripheral resistance that accounts for vessel reactivity. In one embodiment, step 329 may be performed by a computing processor.

In one embodiment, step 331 may include outputting the blood flow characteristics resulting from the simulation of step 329. For example, step 331 may include storing a blood flow characteristic (e.g., flow or pressure at one or more locations) to an electronic storage medium.

FIG. 3C is a block diagram of an exemplary method 340 of taking vessel reactivity into account in modeling drug effects, according to an exemplary embodiment. The method of FIG. 3C may be performed by server systems 106, based on information, images, and data received from physicians 102 and/or third party providers 104 over electronic network 101. Drug treatments may be vasoactive, but the extent to which vessel reactivity may cause blood pressure levels to increase or decrease may be unknown prior to administering the treatment. Method 340 may be used to model and simulate vasoactive aspects of medication.

In one embodiment, step 341 may include receiving, via an electronic storage medium, a coronary artery model of a person in a resting state. Examples of such a model may include a 3D mesh model or a 1D reduced order model. This coronary artery model may be obtained, e.g., via segmentation of a cardiac CT image.

Step 343 may include determining a vessel size at one or more vessel locations for the person in a vasoactive physiological state due to medication. In one embodiment, step 343 may include modeling the altered physiological state of the person via a reduction in vessel stiffness for the coronary artery model. The modeling may include performing a 3D solid mechanics analysis of the vessel wall accounting for active and passive material properties.

In one embodiment, step 345 may include performing a patient-specific blood flow calculation with the model obtained in step 343 to determine one or more blood flow characteristics (e.g., fractional flow reserve) for the person in the vasoactive physiological state. In one embodiment, step 347 may include outputting, e.g., to an electronic storage medium, characteristics of the relative size of the vessel at one or more vessel locations (e.g., the vessel reactivity or flow-mediated dilation). Alternately or in addition, step 347 may include outputting blood flow characteristics observed as a result of the altered physiological state and/or outputting a comparison of the blood flow characteristics for the person at a resting state versus the corresponding blood flow characteristics for that person in a vasoactive physiological state.

The present disclosure may also apply to modeling and studying other vasoactive disorders, including Raynaud's disease, causalgia, hyperhidrosis, claudication, rest pain, ulceration, gangrene, and/or diabetic vascular disease. Furthermore, these techniques may be optionally augmented with corresponding models of cardiac output increase (e.g., during modeling of exercise states) or the effects of gravity on the vascular reactivity of a patient. Gravity modeling may include taking into account gravity as a force in dilating vessels, as well as the effect of venous return, vascular pooling, and AV shunting.

Gravity modeling may also include modeling patients with severe ischemia, e.g., patients for whom ischemic rest pain symptoms typically occur at night when the legs are elevated (and for whom symptoms are relieved by sitting up and hanging the legs down over the side of the bed). Gravity may help deliver blood to a dilated ischemic vascular bed and relieve symptoms of pain. Other gravitational or extrinsic forces that may impact vascular beds of flow distribution may include, for instance, g-force acceleration or deceleration, weightlessness, submersion, and/or pressurization. Similarly, the disclosure may involve modeling reactive effects in cerebrovascular, visceral, or renovascular systems.

Alternatively or additionally, the present disclosure may be useful in relating disease in vessels supplying a patient's legs to regions of reduced flow in the muscles of the lower extremities. In one embodiment, the reduced flow may be observed (e.g., imaged) during or after physical activity. For example, perfusion imaging may be performed using magnetic resonance imaging methods while the patient is exercising on an MR-compatible ergometer. Severity or location of disease in vessels may be determined from observed exercise perfusion values. Treatments may then be formulated based on this understanding of the disease.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A computer-implemented method of treatment selection using vessel size determination, the method comprising:
   receiving image data of one or more blood vessels of a patient, the image data being obtained while the patient's body is at a resting physiological state;
   generating a patient-specific vascular model of the patient's anatomy, including at least one vessel of the patient from the image data obtained while the patient's body is at the resting physiological state;
   determining, by measurement or estimation, an initial vessel size at one or more locations of the at least one vessel of the patient-specific vascular model at the resting physiological state;
   for each of a plurality of possible treatments:
      generating a respective computational model of a mechanical response of at least a portion of a vessel wall of the patient-specific vascular model caused by a change from the resting physiological state to a respective treatment-induced physiological state associated with the possible treatment; and
      determining, via the respective computational model of the mechanical response, respective altered vessel sizes at one or more locations of the patient-specific vascular model corresponding to the one or more locations of the determined initial vessel size, the respective altered vessel sizes associated with the respective treatment-induced physiological state;
   comparing the respective altered vessel sizes associated with each of the plurality of the treatment-induced physiological states with each other; and
   selecting a possible treatment for the patient from amongst the plurality of possible treatments based on the comparison.

2. The computer-implemented method of claim 1, wherein the mechanical response includes a response associated with one or more of a change of a blood flow in the at least one vessel, a change in blood pressure on the vessel wall, or a response to a medication.

3. The computer-implemented method of claim 1, further comprising:
   determining an initial vessel resistance at at least one location in the at least one vessel at the resting physiological state; and
   for each of the possible treatments:
      determining a respective altered vessel resistance at the at least one location in the at least one vessel at the respective treatment-induced physiological state; and
      determining the respective computational model of the mechanical response based on a difference between the initial vessel resistance and the respective altered vessel resistance.

4. The computer-implemented method of claim 1, further comprising:
   for each of the possible treatments, calculating a value of vessel reactivity based on the mechanical response.

5. The computer-implemented method of claim 1, wherein the at least one vessel includes a peripheral artery.

6. The computer-implemented method of claim 1, further comprising:
   for each of the plurality of treatment-induced physiological states, determining a respective blood flow characteristic associated with the treatment-induced physiological state using the determined computational model of the mechanical response of the vessel wall; and
   comparing the respective blood flow characteristics associated with each of the plurality of treatment-induced physiological states with each other, wherein selecting the possible treatment for the patient is further based on the comparison of the respective blood flow characteristics.

7. The computer-implemented method of claim 6, wherein the respective blood flow characteristic includes fractional flow reserve.

8. The computer-implemented method of claim 1, wherein the change from the resting physiological state to the respective treatment-induced physiological state occurs at a location distinct from the at least portion of the vessel wall.

9. A system for treatment selection using vessel size determination, the system comprising:
   at least one data storage device storing instructions for using vessel reactivity in diagnosing or treating disease; and
   at least one processor configured to execute the instructions to perform operations including:
      receiving image data of one or more blood vessels of a patient, the image data being obtained while the patient's body is at a resting physiological state;
      generating a patient-specific vascular model of the patient's anatomy, including at least one vessel of the patient from the image data obtained while the patient's body is at the resting physiological state;
      determining, by measurement or estimation, an initial vessel size at one or more locations of the at least one vessel of the patient-specific vascular model at the resting physiological state;

for each possible treatment of a plurality of possible treatments:

generating a respective computational model of a mechanical response of at least a portion of a vessel wall of the patient-specific vascular model caused by a change from the resting physiological state to a respective treatment-induced physiological state associated with the possible treatment; and determining, via the respective computational model of the mechanical response, respective altered vessel sizes at one or more locations of the patient-specific vascular model corresponding to the one or more locations of the determined initial vessel size, the respective altered vessel sizes associated with the respective treatment-induced physiological state;

comparing the respective altered vessel sizes associated with each of the plurality of the treatment-induced physiological states with each other; and selecting a possible treatment for the patient from amongst the plurality of possible treatments based on the comparison.

10. The system of claim 9, wherein the mechanical response includes a response associated with one or more of a change of a blood flow in the at least one vessel, a change in blood pressure on the vessel wall, or a response to a medication.

11. The system of claim 9, the operations further comprising:

determining an initial vessel resistance at at least one location in the at least one vessel at the resting physiological state; and for each of the possible treatments:

determining a respective altered vessel resistance at the at least one location in the at least one vessel at the respective treatment-induced physiological state; and determining the respective computational model of the mechanical response based on a difference between the initial vessel resistance and the respective altered vessel resistance.

12. The system of claim 9, further comprising:

for each of the possible treatments, calculating a value of vessel reactivity based on the mechanical response.

13. The system of claim 9, wherein the at least one vessel includes a peripheral artery.

14. The system of claim 9, further comprising:

for each of the plurality of treatment-induced physiological states, determining a respective blood flow characteristic associated with the treatment-induced physiological state using the determined computational model of the mechanical response of the vessel wall; and comparing the respective blood flow characteristics associated with each of the plurality of treatment-induced physiological states with each other, wherein selecting the possible treatment for the patient is further based on the comparison of the respective blood flow characteristics.

15. The system of claim 14, wherein the respective blood flow characteristic includes fractional flow reserve.

16. The system of claim 9, wherein the change from the resting physiological state to the respective treatment-induced physiological state occurs at a location distinct from the at least portion of the vessel wall.

17. A non-transitory computer readable medium for use on a computer system containing computer-executable programming instructions for performing a method of treatment selection using vessel size determination, the method comprising:

receiving image data of one or more blood vessels of a patient, the image data being obtained while the patient's body is at a resting physiological state;

generating a patient-specific vascular model of the patient's anatomy, including at least one vessel of the patient from the image data obtained while the patient's body is at the resting physiological state;

determining, by measurement or estimation, an initial vessel size at one or more locations of the at least one vessel of the patient-specific vascular model at the resting physiological state;

for each of a plurality of possible treatments:

generating a respective computational model of a mechanical response of at least a portion of a vessel wall of the patient-specific vascular model caused by a change from the resting physiological state to a respective treatment-induced physiological state associated with the possible treatment; and determining, via the respective computational model of the mechanical response, respective altered vessel sizes at one or more locations of the patient-specific vascular model corresponding to the one or more locations of the determined initial vessel size, the respective altered vessel sizes associated with the respective treatment-induced physiological state;

comparing the respective altered vessel sizes associated with each of the plurality of the treatment-induced physiological states with each other; and selecting a possible treatment for the patient from amongst the plurality of possible treatments based on the comparison.

18. The non-transitory computer readable medium of claim 17, wherein the mechanical response includes a response associated with one or more of a change of a blood flow in the at least one vessel, a change in blood pressure on the vessel wall, or a response to a medication.

19. The non-transitory computer readable medium of claim 17, wherein the method further includes:

determining an initial vessel resistance at at least one location in the at least one vessel at the resting physiological state; and for each of the possible treatments:

determining a respective altered vessel resistance at the at least one location in the at least one vessel at the respective treatment-induced physiological state; and determining the respective computational model of the mechanical response based on a difference between the initial vessel resistance and the respective altered vessel resistance.

20. The non-transitory computer readable medium of claim 17, wherein the change from the resting physiological state to the respective treatment-induced physiological state occurs at a location distinct from the at least portion of the vessel wall.

* * * * *